United States Patent
Parthasaradhi Reddy et al.

(10) Patent No.: US 9,783,542 B2
(45) Date of Patent: Oct. 10, 2017

(54) PROCESS FOR PRALATREXATE

(71) Applicant: Hetero Research Foundation, Hyderabad (IN)

(72) Inventors: Bandi Parthasaradhi Reddy, Hyderbad (IN); Kura Rathnakar Reddy, Hyderbad (IN); Dasari Muralidhara Reddy, Hyderabad (IN); Katham Srinivasa Reddy, Hyderabad (IN); Bandi Vamsi Krishna, Hyderabad (IN)

(73) Assignee: Hetero Research Foundation (IN)

( * ) Notice: Subject to any disclaimer, the term of this patent is extended or adjusted under 35 U.S.C. 154(b) by 0 days.

(21) Appl. No.: 14/436,962

(22) PCT Filed: Nov. 1, 2013

(86) PCT No.: PCT/IN2013/000678
§ 371 (c)(1),
(2) Date: Apr. 20, 2015

(87) PCT Pub. No.: WO2014/068599
PCT Pub. Date: May 8, 2014

(65) Prior Publication Data
US 2015/0252045 A1    Sep. 10, 2015

(30) Foreign Application Priority Data

Nov. 2, 2012 (IN) .......................... 4582/CHE/2012

(51) Int. Cl.
C07C 67/52     (2006.01)
C07C 67/343    (2006.01)
C07D 475/08    (2006.01)

(52) U.S. Cl.
CPC .......... C07D 475/08 (2013.01); C07C 67/343 (2013.01); C07C 67/52 (2013.01)

(58) Field of Classification Search
CPC ....... C07C 67/52; C07C 69/76; C07C 67/343; C07C 67/48; C07D 475/08
See application file for complete search history.

(56) References Cited

U.S. PATENT DOCUMENTS 6,028,071 A * 2/2000 Sirotnak ............. A61K 31/505
                                                       514/249
6,384,264 B1   5/2002 dos Santos Cristiano et al.

FOREIGN PATENT DOCUMENTS

| CN | 103739604 A | 4/2014 |
|---|---|---|
| WO | 2012/061469 A2 | 5/2012 |
| WO | 2013/096800 A1 | 6/2013 |
| WO | 2013/177713 A1 | 12/2013 |
| WO | 2014/016740 A2 | 1/2014 |
| WO | 2014/020553 A1 | 2/2014 |
| WO | 2014/068599 A2 | 5/2014 |

OTHER PUBLICATIONS

Casey ("Advanced Practical Organic Chemistry", Ch. 9, "Working Up the Reaction", p. 141-187, 1990).*
U.S. Appl. No. 61/653,473, p. 1-49, filed May 31, 2012.*
International Search Report for PCT/IN2013/000678 dated Feb. 2, 2015.

* cited by examiner

*Primary Examiner* — Jafar Parsa
*Assistant Examiner* — Amy C Bonaparte
(74) *Attorney, Agent, or Firm* — Cesar Rivise, PC

(57) ABSTRACT

The present invention provides a novel process for the purification of alpha-propargylhomoterephthalic acid dimethyl ester substantially free of homoterephthalic acid dimethyl ester. The present invention also provides a novel process for the purification of pralatrexate.

3 Claims, No Drawings

PROCESS FOR PRALATREXATE

This application claims the benefit of Indian Provisional Patent Application No. 4582/CHE/2012, filed on Nov. 2, 2012, which is incorporated herein by reference.

FIELD OF THE INVENTION

The present invention provides a novel process for the purification of alpha-propargylhomoterephthalic acid dimethyl ester substantially free of homoterephthalic acid dimethyl ester. The present invention also provides a novel process for the purification of pralatrexate.

BACKGROUND OF THE INVENTION

Pralatrexate is chemically, N-(4-{1-[(2,4-diaminopteridin-6-yl)methyl]but-3-yn-1-yl}benzoyl)-L-glutamic acid and has the structural formula:

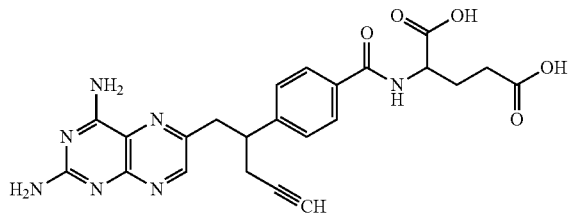 [SMILES: C#CCC(Cc1cnc2nc(N)nc(N)c2n1)c1ccc(C(=O)NC(CCC(=O)O)C(=O)O)cc1]

Pralatrexate is an anti-cancer therapy. It is the first drug approved as a treatment for patients with relapsed or refractory peripheral T-cell lymphoma, or PTCL—a biologically diverse group of aggressive blood cancers. Pralatrexate is currently marketed under the trade name FOLOTYN® by Allos.

Pralatrexate was disclosed in U.S. Pat. Nos. 5,354,751 and 6,028,071.

According to the '071 patent, alpha-propargylhomoterephthalic acid dimethyl ester substantially free of homoterephthalic acid dimethyl ester was obtained by chromatographing alpha-propargylhomoterephthalic acid dimethyl ester residue obtained as part of the reaction between homoterephthalic acid dimethyl ester and propargyl bromide in the presence of tetrahydrofuran and sodium hydride on silica gel using cyclohexane and ethyl acetate (8:1) for the elution.

Pralatrexate was also reported in *J. Med. Chem*, 1993, 36, 2228-2231. According to the paper, pralatrexate is prepared by crystallizing pralatrexate diethyl ester in a mixture of 2-methoxyethanol and water in the presence of sodium hydroxide.

International patent application publication no. WO 2012/061469 ('469 patent) disclosed crystalline Form A, Form B and Form C of pralatrexate. According to the '469 patent, crystalline pralatrexate Form A can be prepared by crystallizing amorphous pralatrexate in formamide.

According to the '469 patent, crystalline pralatrexate Form B can be prepared by crystallizing amorphous pralatrexate in methanol or water.

According to the '469 patent, crystalline pralatrexate Form C can be prepared by crystallizing amorphous pralatrexate in a mixture of methanol and water.

Alpha-propargylhomoterephthalic acid dimethyl ester is a key staring material for the preparation of pralatrexate.

It has been found that the preparation of alpha-propargyl-homoterephthalic acid dimethyl ester substantially free of homoterephthalic acid dimethyl ester by column isolation in the prior art. It is not commercially possible. The present invention makes now available a more efficient process for the purification of alpha-propargylhomoterephthalic acid dimethyl ester substantially free of homoterephthalic acid dimethyl ester by crystallization.

In particular, the present invention is directed to reduce or remove homoterephthalic acid dimethyl ester impurity from alpha-propargylhomoterephthalic acid dimethyl ester. Alpha-propargylhomoterephthalic acid dimethyl ester substantially free of homoterephthalic acid dimethyl ester used to proceed in the synthesis is very important in order avoid the sequential formation of homoterephthalic acid dimethyl ester during the transformation lading to the pralatrexate.

10-Propargyl-4-deoxy-4-amino-10-dezapteroic acid and 10-deazaaminopterin are potential impurities in pralatrexate formed by procedures described in the art.

The chemical formula of 10-propargyl-4-deoxy-4-amino-10-dezapteroic acid impurity may be represented as:

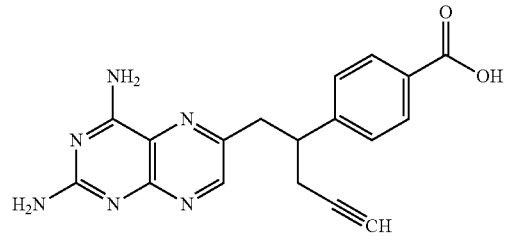 [SMILES: C#CCC(Cc1cnc2nc(N)nc(N)c2n1)c1ccc(C(=O)O)cc1]

The chemical formula of 10-deazaaminopterin impurity may be represented as:

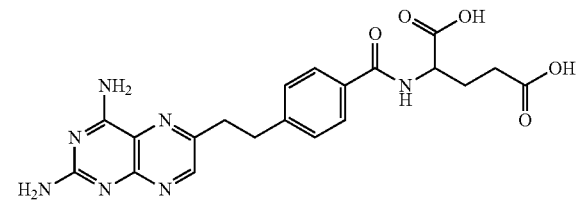 [SMILES: Nc1nc(N)c2nc(CCc3ccc(C(=O)NC(CCC(=O)O)C(=O)O)cc3)cnc2n1]

In particular, the present invention is directed to reduce or remove 10-propargyl-4-deoxy-4-amino-10-dezapteroic acid and 10-deazaaminopterin impurities from pralatrexate. The process of the invention may be used for obtaining pralatrexate in high purity with less than 0.1% of any individual impurities, in particular 10-propargyl-4-deoxy-4-amino-10-dezapteroic acid and 10-deazaaminopterin impurities.

Thus, one object of the present invention is to provide a novel process for the purification of alpha-propargylhomoterephthalic acid dimethyl ester substantially free of homoterephthalic acid dimethyl ester.

Another object of the present invention is to provide a novel process for the purification of pralatrexate.

SUMMARY OF THE INVENTION

In one aspect, the present invention provides a novel process for the purification of alpha-propargylhomoterephthalic acid dimethyl ester substantially free of homoterephthalic acid dimethyl ester, which comprises crystallizing the alpha-propargylhomoterephthalic acid dimethyl ester substantially free of homoterephthalic acid dimethyl ester from a solution of alpha-propargylhomoterephthalic acid dimethyl ester containing homoterephthalic acid dimethyl ester in an ether solvent, a hydrocarbon solvent or mixture thereof.

In another aspect, the present invention provides a novel process for the purification of pralatrexate, which comprises:
a) dissolving pralatrexate in an ether solvent;
b) heating the solution above 50° C.;
c) adding water to the solution above 50° C.;
d) isolating the solid;
e) dissolving the solid in dimethylformamide, dimethylacetamide, dimethyl sulfoxide or mixture thereof;
f) adding an alcoholic solvent to the solution; and
g) isolating the pure pralatrexate.

DETAILED DESCRIPTION OF THE INVENTION

The term "room temperature" refers to temperature at about 25 to 35° C.

According to one aspect of the present invention, there is provided a novel process for the purification of alpha-propargylhomoterephthalic acid dimethyl ester substantially free of homoterephthalic acid dimethyl ester, which comprises crystallizing the alpha-propargylhomoterephthalic acid dimethyl ester substantially free of homoterephthalic acid dimethyl ester from a solution of alpha-propargylhomoterephthalic acid dimethyl ester containing homoterephthalic acid dimethyl ester in an ether solvent, a hydrocarbon solvent or mixture thereof.

The ether solvent used in the process may preferably be a solvent or a mixture of solvents selected from tetrahydrofuran, methyl tetrahydrofuran, methyl tert-butyl ether, ethyl tert-butyl ether, 1,4-dioxane, diisopropyl ether, diethyl ether and tetrahydropyran. More preferably the ether solvent is diisopropyl ether.

The hydrocarbon solvent used in the process may preferably be a solvent or a mixture of solvents selected from hexane, cyclohexane, n-hexane, heptane, benzene, toluene and xylene. More preferably the hydrocarbon solvent is hexane.

Crystallization of alpha-propargylhomoterephthalic acid dimethyl ester substantially free of homoterephthalic acid dimethyl ester from the solution of alpha-propargylhomoterephthalic acid dimethyl ester containing homoterephthalic acid dimethyl ester in an ether solvent, a hydrocarbon solvent or mixture thereof can be performed by conventional methods such as cooling, partial removal of solvents, seeding or a combination thereof. The separated solid may be collected by the method known such as centrifugation or filtration.

According to another aspect of the present invention, there is provided a novel process for the purification of pralatrexate, which comprises:
a) dissolving pralatrexate in an ether solvent;
b) heating the solution above 50° C.;
c) adding water to the solution above 50° C.;
d) isolating the solid;
e) dissolving the solid in dimethylformamide, dimethylacetamide, dimethyl sulfoxide or mixture thereof;
f) adding an alcoholic solvent to the solution; and
g) isolating the pure pralatrexate.

The term "pure pralatrexate" refers to pralatrexate having the purity greater than about 98.5% by weight, preferably greater than about 99% by weight, and more preferably greater than about 99.5% by weight.

The ether solvent used in step (a) may preferably be a solvent or a mixture of solvents selected from teterahydrofuran, 1,4-dioxane, tert-butyl methyl ether and diethyl ether, and more preferably the ether solvent is teterahydrofuran.

The reaction in step (b) and step (c) may preferably be carried out at 55 to 65° C.

Isolation of the solid in step (d) can be performed by conventional methods such as cooling, removal of solvents, concentrating the reaction mass, adding an anti-solvent, extraction with a solvent and the like.

The alcoholic solvent used in step (f) may preferably be a solvent or a mixture of solvents selected from methanol, ethanol, isopropanol and n-butanol. More preferably the alcoholic solvent is ethanol.

Pure pralatrexate may be isolated in step (g) by methods known such as filtration or centrifugation.

The contents of pralatrexate and the impurities are determined by High performance liquid chromatography (HPLC).

The invention will now be further described by the following example, which is illustrative rather than limiting.

EXAMPLES

Example 1

Preparation of Alpha-propargylhomoterephthalic Acid Dimethyl Ester

Sodium hydride (60 gm; 60%) was added to tetrahydrofuran (1500 ml) at room temperature and then cooled to 10 to 15° C. To the solution was added a solution of homoterephthalic acid dimethyl ester (250 gm) in tetrahydrofuran (250 ml) slowly for 15 minutes. The reaction mass was then cooled to 0 to −5° C. and then added propargyl bromide (130 gm) in tetrahydrofuran (125 ml) slowly for 15 minutes at 0 to −5° C. The reaction mass was maintained for 2 hours at 0 to −5° C. and then added methanol (50 ml). The temperature of the reaction mass was raised to room temperature and then added water (1500 ml) and diisopropyl ether (2500 ml), and then the layers were separated. The organic layer were dried with sodium sulfate and then concentrated to obtain 275 gm of alpha-propargylhomoterephthalic acid dimethyl ester.

Chromatographic purity of alpha-propargylhomoterephthalic acid dimethyl ester: 62.0%;

Content of homoterephthalic acid dimethyl ester: 12.0%.

Example 2

Purification of Alpha-propargylhomoterephthalic Acid Dimethyl Ester

Alpha-propargylhomoterephthalic acid dimethyl ester (275 gm; HPLC Purity: 62.0%) as obtained in example 1 was dissolved in a mixture of hexane (1200 ml) and diisopropyl ether (65 ml) at room temperature. The solution was stirred for 15 hours at room temperature and filtered. The solid obtained was dried to obtain 175 gm of alpha-propargylhomoterephthalic acid dimethyl ester.

Chromatographic purity of alpha-propargylhomoterephthalic acid dimethyl ester: 74.6%;

Content of homoterephthalic acid dimethyl ester: 0.4%.

Example 3

Preparation of 10-propargyl-10-deazaminopterin Diethyl Ester

Step-I: Preparation of 10-propargyl-10-carbomethoxy-4-deoxy-4-amino-10-deazapteroic Acid Methyl Ester Sodium hydride (120 gm; 60%) was added to dimethylformamide (750 ml) at room temperature and then cooled to 0 to −5° C. To the solution was added a solution of alpha-propargylhomoterephthalic acid dimethyl ester (250 gm) in dimethylformamide (750 ml) slowly for 15 minutes. The reaction mixture was maintained for 30 minutes at 0 to −5° C. and then cooled to −20 to −25° C. To the reaction mixture was added 6-bromomethyl-pteridine-2,4-diamine (300 gm) in dimethylformamide (1500 ml) slowly for 30 minutes. The reaction mass was maintained for 2 hours at −20 to −25° C. and then added methanol (300 ml). The temperature of the reaction mass was raised to room temperature and then added water (15000 ml) and diisopropyl ether (1500 ml). The contents were stirred for 2 hours at room temperature and filtered. The solid obtained was dried to obtain 198 gm of 10-propargyl-10-carbomethoxy-4-deoxy-4-amino-10-deazapteroic acid methyl ester.

Step-II: Preparation of 10-propargyl-10-carboxy-4-deoxy-4-amino-10-deazapteroic Acid 2-Methoxyethanol (775 gm) was added to 10-propargyl-10-carbomethoxy-4-deoxy-4-amino-10-deazapteroic acid methyl ester (155 gm) at room temperature and then cooled to 15 to 20° C. To the reaction mixture was added a solution of sodium hydroxide (120 gm) in water (930 ml) and maintained for 4 hours at room temperature. The pH of the reaction mass was is adjusted to 4.5 to 4.6 with acetic acid (50%) and then added water (3100 ml). The reaction mass was stirred for 2 hours, filtered and then dried to obtain 125 gm of 10-propargyl-10-carboxy-4-deoxy-4-amino-10-deazapteroic acid.

Step-III: Preparation of 10-propargyl-4-deoxy-4-amino-10-deazapteroic Acid

10-Propargyl-10-carboxy-4-deoxy-4-amino-10-deazapteroic acid (135 gm) was added to dimethyl sulfoxide (1350 ml) at 120 to 125° C. and maintained for 45 minutes at 120 to 125° C. The reaction mass was poured into water (3000 ml), maintained for 24 hours at room temperature and filtered to obtain a wet solid. To the wet solid was basified and then acetified, and maintained for 2 hours at room temperature. The separated solid was filtered and then dried to obtain 56 gm of 10-propargyl-4-deoxy-4-amino-10-deazapteroic acid.

Step-IV: Preparation of 10-propargyl-10-deazaminopterin Diethyl Ester

Dimethylformamide (112 ml) was added to 10-propargyl-4-deoxy-4-amino-10-deazapteroic acid (14 gm) and stirred for 15 minutes. To the reaction mixture was added triethylamine (14 ml) and then cooled to 0 to −5° C. A solution of (benzotriazol-1-yloxy)tris(dimethylamino)phosphonium hexafluorophosphate (21 gm) in dimethylformamide (28 ml) was added to the reaction mixture and maintained for 1 hour at 0 to −5° C. To the reaction mixture was added L-glutamic acid diethyl ester (10 gm) in dimethylformamide (28 ml) slowly, maintained for 2 hours at −10 to −15° C. and filtered. The pH of the filtrate obtained was adjusted with sodium hydroxide solution and then added water (700 ml) slowly for 45 minutes. The reaction mass was maintained for 2 hours at room temperature, filtered and then dried to obtain 14 gm of 10-propargyl-10-deazaminopterin diethyl ester.

Example 4

Preparation of Pralatrexate

10-Propargyl-10-deazaminopterin diethyl ester (40 gm) was dissolved in tetrahydrofuran (320 ml) at room temperature. The solution was then cooled to 15 to 20° C. and added a solution of sodium hydroxide (24 gm) in water (400 ml) slowly for 15 minutes. The reaction mass was maintained for 45 minutes at 15 to 20° C. and then added a mixture of tetrahydrofuran (200 ml) and ethyl acetate (200 ml). The layers were separated and to the aqueous layer was added water (80 ml). The separated aqueous layer was then concentrated and pH was adjusted to 4.7 to 4.8 with acetic acid (10%). The contents were stirred for 1 hour at room temperature and filtered. The solid obtained was then dried to obtain 28 gm of pralatrexate.

Chromatographic purity of pralatrexate: 98.5%;
Content of 10-propargyl-4-deoxy-4-amino-10-dezapteroic acid: 0.3%;
Content of 10-deazaaminopterin: 0.5%;

Example 5

Purification of Pralatrexate

The pralatrexate (28 gm: HPLC Purity: 98.5%) as obtained in example 4 was dissolved in tetrahydrofuran (400 ml) and then heated to 60° C. To the contents were added water (200 ml) at 60° C. and then cooled to 5 to 10° C. The contents were stirred for 2 hours 30 minutes at 5 to 10° C., filtered and then dried to obtain a solid. The solid was dissolved in dimethyl sulfoxide (138 ml) and then stirred to obtain a clear solution. The solution was filtered through celite bed and then added ethanol (690 ml) slowly for 1 hour. The contents were stirred for 1 hour at room temperature, filtered and then dried to obtain 20 gm of pure pralatrexate.

Chromatographic purity of pralatrexate: 99.5%;
Content of 10-propargyl-4-deoxy-4-amino-10-dezapteroic acid: 0.06%;
Content of 10-deazaaminopterin: 0.08%.

We claim:

1. A process for the purification of alpha-propargylhomoterephthalic acid dimethyl ester from homoterephthalic acid dimethyl ester, which comprises crystallizing the alpha-propargylhomoterephthalic acid dimethyl ester from a solution of alpha-propargylhomoterephthalic acid dimethyl ester containing homoterephthalic acid dimethyl ester
   in an ether solvent, a hydrocarbon solvent or a mixture thereof,
   wherein the homoterephthalic acid dimethyl ester content of the purified alpha-propargylhomoterephthalic acid dimethyl ester is not more than 0.4%.

2. The process as claimed in claim 1, wherein the ether solvent used in the process is a solvent or a mixture of solvents selected from the group consisting of tetrahydrofuran, methyl tetrahydrofuran, methyl tert-butyl ether, ethyl tert-butyl ether, 1,4-dioxane, diisopropyl ether, diethyl ether and tetrahydropyran.

3. The process as claimed in claim 1, wherein the hydrocarbon solvent used in the process is a solvent or a mixture of solvents selected from the group consisting of hexane, cyclohexane, n-hexane, heptane, benzene, toluene and xylene.

* * * * *